(12) United States Patent
Kilim et al.

(10) Patent No.: US 9,241,632 B2
(45) Date of Patent: Jan. 26, 2016

(54) SYNCHRONIZATION OF WIRELESS CATHETERS

(75) Inventors: Nahum Kilim, Haifa (IL); Assaf Govari, Haifa (IL); Andres Claudio Altmann, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 116 days.

(21) Appl. No.: 13/186,626

(22) Filed: Jul. 20, 2011

(65) Prior Publication Data

US 2013/0023746 A1   Jan. 24, 2013

(51) Int. Cl.
*A61B 5/0402* (2006.01)
*H04J 3/06* (2006.01)
*A61B 5/00* (2006.01)
*A61B 5/042* (2006.01)

(52) U.S. Cl.
CPC .............. *A61B 5/0006* (2013.01); *A61B 5/0015* (2013.01); *A61B 5/0031* (2013.01); *H04J 3/06* (2013.01); *H04J 3/0635* (2013.01); *H04J 3/0647* (2013.01); *H04J 3/0658* (2013.01); *H04J 3/0661* (2013.01); *H04J 3/0667* (2013.01); *A61B 5/042* (2013.01); *A61B 5/0422* (2013.01); *A61B 5/6852* (2013.01)

(58) Field of Classification Search
CPC ......... H04J 3/06; H04J 3/0635; H04J 3/0647; H04J 3/0658; H04J 3/0661; H04J 3/0667
USPC .............. 600/509; 607/59, 60; 370/250, 503
See application file for complete search history.

(56) References Cited

U.S. PATENT DOCUMENTS

| 4,005,266 A | 1/1977 | Lehr et al. |
|---|---|---|
| 6,441,747 B1 | 8/2002 | Khair et al. |
| 6,897,788 B2 | 5/2005 | Khair et al. |
| 7,729,742 B2 | 6/2010 | Govari |
| 8,396,563 B2 | 3/2013 | Reinke et al. |
| 2003/0120150 A1 | 6/2003 | Govari |

(Continued)

FOREIGN PATENT DOCUMENTS

| CN | 101675900 | 3/2010 |
|---|---|---|
| CN | 101997648 | 3/2011 |

(Continued)

OTHER PUBLICATIONS

Extended European Search Report dated Nov. 26, 2012 from related European Application No. 12177016.8.

(Continued)

*Primary Examiner* — Allen Porter, Jr.
(74) *Attorney, Agent, or Firm* — Louis J. Capezzuto

(57) ABSTRACT

A method includes disposing multiple medical probes to acquire physiological data concurrently from a living body. The data is sent from the multiple medical probes by transmitting over wireless channels respective sequences of data packets that are marked with respective packet numbers. A synchronization signal that is broadcast to the multiple probes is received in the probes. In response to receiving the synchronization signal, the packet numbers that are to be assigned in the probes to subsequent data packets in the respective sequences are reset.

11 Claims, 3 Drawing Sheets

(56) References Cited

U.S. PATENT DOCUMENTS

| | | |
|---|---|---|
| 2009/0088821 A1* | 4/2009 | Abrahamson .................. 607/60 |
| 2009/0131762 A1 | 5/2009 | Pelzek et al. |
| 2010/0042010 A1* | 2/2010 | Dekker et al. ................ 600/523 |
| 2010/0056871 A1 | 3/2010 | Govari et al. |
| 2011/0190850 A1 | 8/2011 | Reinke et al. |

FOREIGN PATENT DOCUMENTS

| | | |
|---|---|---|
| EP | 2 158 841 A2 | 3/2010 |
| WO | WO 2008/026970 | 3/2008 |
| WO | WO 2008/129510 A2 | 10/2008 |
| WO | WO 2011/085394 A2 | 7/2011 |

OTHER PUBLICATIONS

Chinese Office Action for CN201210254519.3 dated Jun. 5, 2015.

Search Report issued by the Office of the People's Republic of China dated Apr. 22, 2015 for corresponding Application No. 20121025419.3.

Search Report issued by the Office of the People's Republic of China dated Jun. 5, 2009 for corresponding Application No. 20121025419.3.

Search Report issued by the Office of the People's Republic of China dated Sep. 25, 2015 for corresponding Application No. 20121025419.3.

* cited by examiner

SYNCHRONIZATION OF WIRELESS CATHETERS

FIELD OF THE INVENTION

The present invention relates generally to medical probes, and particularly to methods and systems for synchronizing wireless medical probes.

BACKGROUND OF THE INVENTION

Some intra-body medical probes, such as cardiac catheters, transmit data over a wireless channel in order to reduce cabling. Several methods and systems for controlling such probes are known in the art. For example, U.S. Patent Application Publication 2010/0056871, whose disclosure is incorporated herein by reference, describes a method for device control. The method includes bringing a plurality of medical devices into contact with a body of a patient. The medical devices are coupled to communicate with a console via a digital interface. A message is transmitted over the digital interface from the console, to be received simultaneously by the plurality of the medical devices. The medical devices are synchronized with one another responsively to receiving the message. In some embodiments, signals are sampled using a respective internal clock in each of the medical devices, and the medical devices are synchronized by resetting the internal clock.

SUMMARY OF THE INVENTION

An embodiment of the present invention that is described herein provides a method including disposing multiple medical probes to acquire physiological data concurrently from a living body. The data is sent from the multiple medical probes by transmitting over wireless channels respective sequences of data packets that are marked with respective packet numbers. A synchronization signal that is broadcast to the multiple probes is received in the probes. In response to receiving the synchronization signal, the packet numbers that are to be assigned in the probes to subsequent data packets in the respective sequences are reset.

In some embodiments, disposing the probes includes acquiring the data in each probe in accordance with a respective internal clock signal that is free-running irrespective of the synchronization signal. In an embodiment, disposing the probes includes acquiring the data from multiple sensors in a given probe by scanning the sensors in a predefined cycle, and the method includes resetting the cycle in the given probe in response to receiving the synchronization signal.

In some disclosed embodiments, the method includes transmitting an acknowledgement packet from each probe in response to receiving the synchronization signal at the probe, and time-synchronizing the data sent from the multiple probes based on respective acknowledgement packets transmitted by the probes. In an embodiment, transmitting the acknowledgement packet includes indicating in each acknowledgement packet a respective time offset at which the synchronization signal was received at the respective probe, relative to a data packet produced by the probe. Time-synchronizing the data may include synchronizing the data based on multiple time offsets indicated in the acknowledgement packets transmitted by the probes.

In a disclosed embodiment, time-synchronizing the data includes estimating, based on multiple time offsets indicated in the acknowledgement packets transmitted by the probes, a time period during which the data is not synchronized, and discarding the data belonging to the estimated time period. In another embodiment, transmitting the acknowledgement packet includes indicating in each acknowledgement packet a respective last packet number of a last data packet that was transmitted from the respective probe before reception of the synchronization signal, and time-synchronizing the data includes synchronizing the data based on multiple last packet numbers indicated in the acknowledgement packets transmitted by the probes.

In yet another embodiment, the method includes presenting the time-synchronized data to an operator. In still another embodiment, the method includes evaluating a predefined criterion, and transmitting the synchronization signal upon meeting the criterion. Evaluating the criterion may include estimating a time difference between the multiple probes based on the received data packets, and comparing the time difference to a threshold. In an embodiment, transmitting the synchronization signal includes sending the synchronization signal at periodic intervals. In a disclosed embodiment, the probes include intracardiac catheters, and the sensors include electrodes that measure electrical signals in a heart.

There is additionally provided, in accordance with an embodiment of the present invention, a medical probe for use in a set of multiple medical probes operating concurrently. The probe includes one or more sensors and circuitry. The sensors are configured to acquire physiological data from a living body with which the probe is in contact. The circuitry is configured to send the data from the probe by transmitting over a wireless channel a sequence of data packets that are marked with respective packet numbers, to receive a synchronization signal that is broadcast to the multiple probes, and, in response to receiving the synchronization signal, to reset the packet numbers that are assigned in the probe to subsequent data packets in the sequence.

There is also provided, in accordance with an embodiment of the present invention, a system including multiple medical probes and a central control unit. Each probe is configured to acquire physiological data from a living body with which the probe is in contact, to send the data from the probe by transmitting over a wireless channel a sequence of data packets that are marked with respective packet numbers, to receive a synchronization signal that is broadcast to the multiple probes, and, in response to receiving the synchronization signal, to reset the packet numbers that are assigned in the probe to subsequent data packets in the sequence. The central control unit is configured to transmit the synchronization signal, to receive multiple respective sequences of the data packets from the multiple probes, to time-synchronize the data transmitted in the data packets and to output the time-synchronized data.

The present invention will be more fully understood from the following detailed description of the embodiments thereof, taken together with the drawings in which:

DETAILED DESCRIPTION OF EMBODIMENTS

Overview

Figure 1:
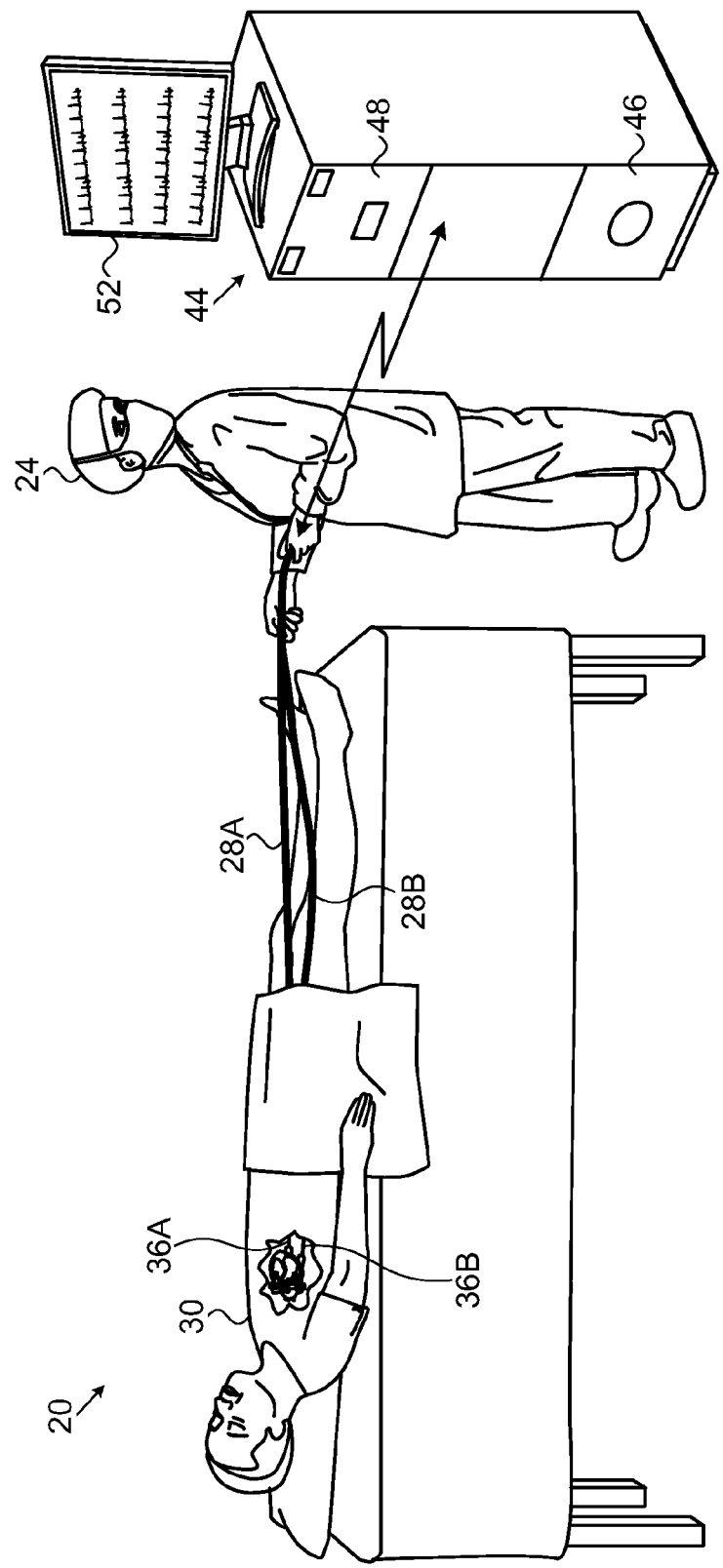
FIG. 1 is a schematic, pictorial illustration of a catheterization system that uses multiple catheters, in accordance with an embodiment of the present invention.

Embodiments of the present invention that are described hereinbelow provide improved methods and systems for synchronizing physiological data that is acquired concurrently by multiple wireless medical probes. In the disclosed embodiments, multiple probes are inserted into a patient's body. Each probe measures the data using one or more sensors, e.g., electrodes, digitizes the measured data and transmits the data over a wireless channel to a central control unit. The central control unit synchronizes the data that it receives from the different probes, and outputs the synchronized data.

In an example application, the probes comprise cardiac catheters, each comprising one or more electrodes that measure electrical signals at various points in the patient's heart. The measured electrical data is transmitted from the multiple catheters, and the central control unit displays the data from the multiple electrodes (referred to as "ECG channels") graphically to a physician.

In many applications it is important to time-synchronize the data that is received from the multiple probes. In the above-described intracardiac electrogram application, for example, the multiple ECG channels are to be displayed to the physician synchronized with one another. On the other hand, since the data from each probe undergoes separate processing and propagation, data from different probes may be available for display at different time delays.

In some embodiments, each probe transmits the data in a sequence of data packets marked with respective packet numbers. The central control unit synchronizes the data from the different probes by broadcasting a synchronization signal to the probes. Upon receiving the synchronization signal, each probe resets the packet numbers that are assigned by the probe to subsequent data packets. When the probe comprises multiple electrodes that are sampled and multiplexed in a certain predefined cycle, the probe also resets the electrode sampling cycle in response to the synchronization signal. Each probe responds to the synchronization signal by transmitting an acknowledgment packet, and the central control unit synchronizes the data from the various probes based on the acknowledgement packets received from the probes.

In an embodiment, the data in every data packet originates from the same predefined sampling pattern of the probe electrodes. In other words, the data samples in each packet begin at a predefined electrode and continue cycling over the electrodes, possibly multiple times, according to a predefined multiplexing order. Thus, the position of a given data sample in the packet is indicative of the sample's position in the electrode sampling pattern, and in particular of the electrode from which the sample was acquired.

In these embodiments, the acknowledgement packet comprises an offset parameter that indicates the time offset at which the synchronization signal was received at the probe, relative to the data packet that is currently being formatted. The offset parameters that are received from the different probes enable the central control unit to align the sequences of data packets from the different probes with one another. In one embodiment, the central control unit identifies the largest offset parameter value and discards any data, from any probe, that precedes this offset. After synchronization, the synchronized data is output, e.g., displayed to the physician.

The methods and systems described herein enable the central control unit to synchronize data from multiple wireless probes, even though the data may have different time delays. Typically, synchronizing the data does not involve resetting or otherwise interfering with the internal clock signals of the probes that are used for sampling the electrodes. As such, the disclosed techniques are simple to implement and do not waste sampling time due to clock synchronization.

System Description

FIG. 1 is a schematic, pictorial illustration of a catheterization system 20 that uses multiple catheters, in accordance with an embodiment of the present invention. In the example of FIG. 1, system 20 comprises two catheters 28A and 28B. In alternative embodiments, however, the system may comprise any other suitable number of catheters or other medical probes, which sense physiological data concurrently in a patient's body.

A physician 24 (or other operator) inserts catheters 28A and 28B into the body of a patient 30. Each catheter has a proximal end that is handled by the physician, and a distal end that is navigated through the patient body. The distal ends of catheters 28A and 28B are denoted 36A and 36B, respectively. Catheters 28A and 28B communicate with a driver unit 48 of a control console 44 using wireless communication. In the embodiment described herein, the catheters are inserted into the patient's heart and used for intracardiac electrogram measurement, for ablation and/or for creating electrophysiological maps of one or more heart chambers. Alternatively, catheter 28 may be used, mutatis mutandis, for other therapeutic and/or diagnostic purposes in the heart or in other body organs.

The distal end of each catheter comprises one or more sensors that sense certain physiological data in the vicinity of the distal end, e.g., electrodes that sense electrical signals in the patient's heart. Although the embodiments described herein refer mainly to electrodes, the disclosed techniques can be used with any other suitable type of sensor.

The catheters comprise wireless catheters, which transmit signals that carry the data sensed by the electrodes over a wireless channel. The use of wireless catheters eliminates at least some of the cabling that runs through the catheter, and therefore reduces the catheter diameter. In the example of FIG. 1, the catheters communicate with console 24 exclusively using wireless communication. In alternative embodiments, the catheters may still be connected to the console using cables, e.g., for transferring electrical power to the catheter distal ends or for any other purpose.

System 20 comprises a central control unit (CCU) 46, which receives the wireless signals transmitted from catheters 28A and 28B. Unit 46 extracts the data from the received signals and displays the data to physician 24 on a display 52. In the present example, display 52 shows multiple ECG channels, which are acquired by multiple electrodes in catheters 28A and 28B. In particular, central control unit 46 synchronizes the data received from the different catheters using methods that are explained in detail below. Unit 46 displays the synchronized data (ECG channels in the present example) to physician 24 using display 52.

Figure 2:
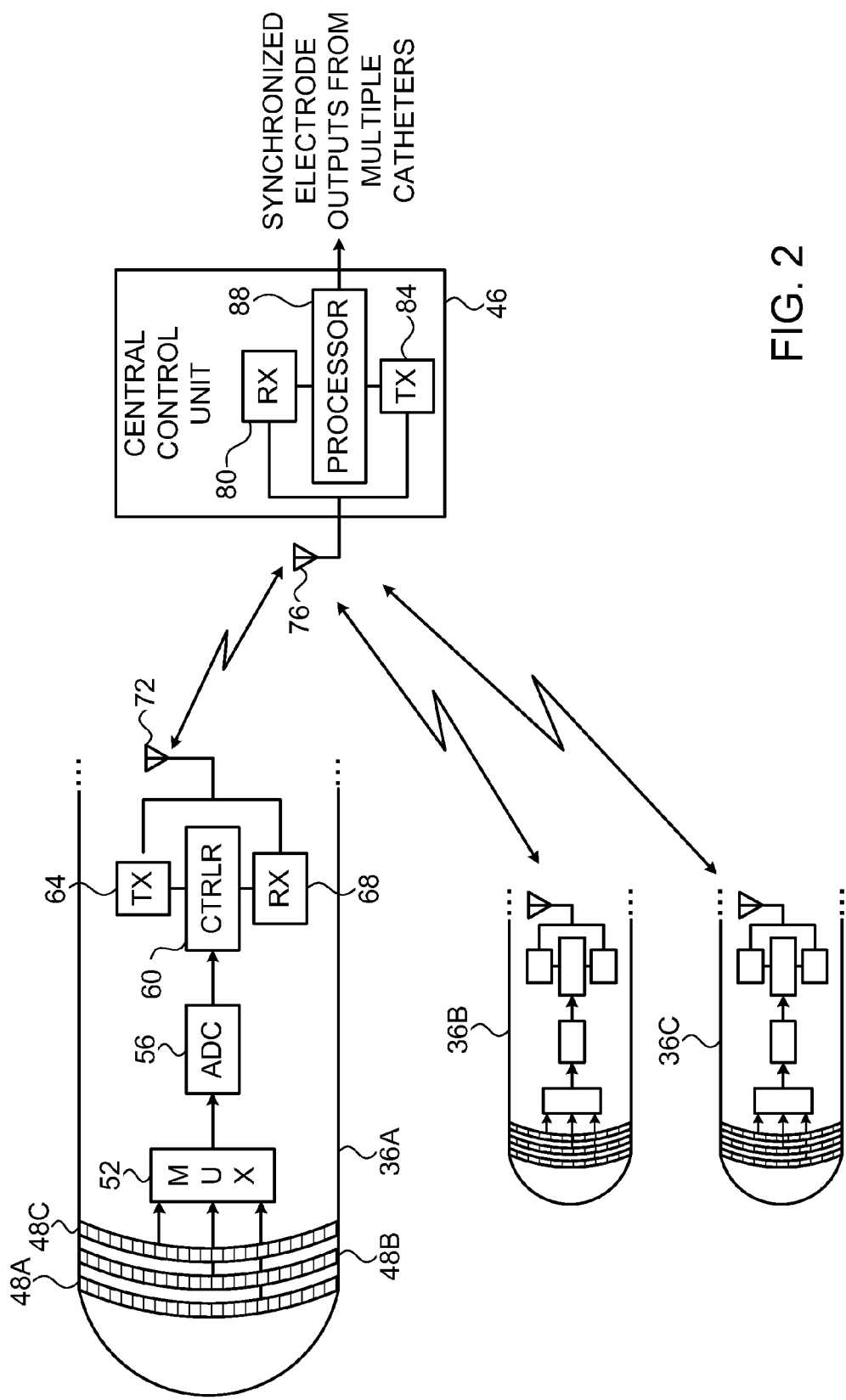
FIG. 2 is a block diagram that schematically illustrates a catheterization system that uses multiple catheters, in accordance with an embodiment of the present invention.

FIG. 2 is a block diagram that schematically illustrates details of certain elements of system 20, in accordance with an embodiment of the present invention.

The figure shows distal ends 36A . . . 36C of three wireless catheters that communicate with central control unit 46. Distal end 36A is shown in greater detail for the sake of clarity. The distal ends of the other catheters typically have a similar configuration.

Distal end 36A comprises multiple electrodes. In the present example, the distal end comprises three ECG electrodes 48A . . . 48C that sense the patient's ECG. In alternative embodiments, the distal end may comprise any desired number of electrodes, or even a single electrode. Additionally or alternatively to using electrical signal electrodes, electrodes of any other suitable type can be used. The locations and mechanical configurations of electrodes 48A . . . 48C shown in FIG. 2 is chosen purely by way of example, and any other suitable configuration can be used. Each electrode produces an analog value (voltage or current) that is indicative of the sensed parameter.

In addition to the electrodes, the catheter distal end comprises circuitry, in the present example comprising a multiplexer (MUX) 52, an Analog-to-Digital Converter (ADC) 56, a controller 60, a transmitter 64, a receiver 68 and an antenna 72. In an example embodiment, some or all of these elements may be implemented on a single Printed Circuit Board (PCB), in a single Integrated Circuit (IC), or in any other suitable configuration.

MUX 52 alternates between the electrode and multiplexes the analog values they produce. ADC 56 digitizes the multiplexed analog values so as to produce digital samples. Thus, the ADC produces a data stream that alternates between the electrodes. Controller 60 processes the data stream produced by ADC 56. In particular, controller 60 formats the data in a sequence of data packets, and provides the data packets to transmitter 64. Transmitter 64 produces Radio Frequency (RF) signals that carry the data packets, and transmits the RF signals via antenna 72 to unit 46.

Central control unit 46 comprises an antenna 76, a receiver 80, a transmitter 84 and a processor 88. Receiver 80 receives the RF signals from the different catheters via antenna 76. Receiver 80 extracts the data packets from the received RF signals, and provides the data packets to processor 88. Processor 88 extracts the data from the data packets and displays the data obtained from the different catheters (ECG channels in the present example) on display 52.

Transmitter 80 in unit 46 and receivers 68 in the multiple catheters are used for broadcasting a synchronization signal from unit 46 to the catheters, as part of a synchronization process that is described in detail below.

The configurations of system 20, central control unit 46 and catheters 28A and 28B shown in FIGS. 1 and 2 are example configurations that are chosen purely for the sake of conceptual clarity. In alternative embodiments, any other suitable configurations can be used. Processor 88 typically comprises a general-purpose processor, which is programmed in software to carry out the functions that are described herein. The software may be downloaded to processor 88 in electronic form, over a network, for example, or it may be provided on non-transitory tangible media, such as optical, magnetic or electronic memory media. For example, unit 46 may be implemented on a Personal Computer (PC) running a suitable operating system such as Microsoft Windows. Alternatively, some or all of the functions of processor 88 may be carried out by dedicated or programmable digital hardware components.

Synchronizing Multiple Catheters

In a practical implementation, the data packets arriving from different catheters may experience different time delays en-route to processor 88. The differences in time delay may be caused, for example, by different processing delays in the elements of the catheter (e.g., transmitters 64 and controllers 60), by different processing delays in the elements of unit 46 (e.g., receiver 80 and processor 88), or for any other reason. On the other hand, in many applications it is important to time-synchronize the data from the different catheters with one another, for example in order to display them to physician 24 in a synchronized manner. In some embodiments, system 20 carries out a synchronization process that synchronizes the data received by unit 46 from the different catheters.

Typically, transmitter 64 in each catheter transmits the data to unit 46 in a sequence of data packets. The data packets in the sequence are marked with respective packet numbers, e.g., sequentially increasing numbers. Each data packet carries data that is acquired from one or more cycles of MUX 56 over the catheter electrodes. In an example embodiment, the catheter comprises ten electrodes, and each data packet carries two hundred samples originating from twenty successive multiplexing cycles over the electrodes. In some embodiments, the data in every data packet begins from the same point in the sampling pattern of the electrodes. In other words, the data samples in every packet begin at a predefined electrode and continue cycling over the electrodes according to a predefined multiplexing order.

In some embodiments, processor 88 of central control unit 46 synchronizes catheters 28 by broadcasting a synchronization signal to the catheters using transmitter 84 and antenna 76. In each catheter, the synchronization signal is received via antenna 72 by receiver 68. In each catheter, receiver 68 notifies controller 60 that a synchronization signal has been received. The notification may be implemented, for example, using a hardware interrupt or any other suitable mechanism.

Upon receiving the notification, processor 60 carries out several actions. The processor resets the packet numbering that is assigned to subsequent data packet. In an example embodiment, the processor resets the packet numbering to zero, i.e., assigns subsequent data packets packet numbers that restart from zero. Additionally, processor 88 resets the sampling cycle of the electrodes by MUX 52. In addition, processor 60 transmits an acknowledgement packet to unit 46, using transmitter 64 and antenna 72. The packet number of the acknowledgement packet is still assigned according to the previous numbering sequence, i.e., before resetting.

Typically, the acknowledgement packet comprises an indication that the synchronization signal has indeed been received by the catheter, as well as one or more synchronization parameters. In some embodiments, the acknowledgement packet comprises an offset parameter that indicates the time at which the synchronization signal was received at the catheter, relative to the timing (e.g., beginning) of the data packet that is currently being formatted.

As explained above, every data packet begins in the same phase of the sampling pattern - e.g., at a data sample from the same electrode. Thus, the offset parameter indicates which electrode was sampled at the time of arrival of the synchronization signal. The most recently sampled electrode can be found, for example, by dividing the offset parameter by the length of the sampling pattern and taking the remainder. In alternative embodiments, any other suitable synchronization parameter may be used.

Processor 88 of unit 46 receives the acknowledgement packets from the different catheters via antenna 76 and receiver 80. The processor synchronizes subsequent data packets from the multiple catheters using based on the acknowledgement packets. In some embodiments, processor waits until the acknowledgement packets from all catheters have been received, and then clears the queues or other data structures used for buffering the received data.

In an embodiment, processor 88 extracts the offset parameters from the acknowledgement packets, and uses these parameters to determine a time until which subsequent data packets may be invalid. In an example embodiment, processor 88 identifies the highest packet number among the packet numbers of the acknowledgement packets. The processor extracts the offset parameter from this acknowledgement packet. Using this value, the processor determines which data packets may be invalid, i.e., non-synchronized.

Processor 88 discards the invalid data packets, and begins to store and display only data packets that are later than the above-described time. From this point, processor 88 is able to align the data acquired by the different electrodes in the different catheters, since the exact time offset of the data relative to the synchronization signal is known.

In some embodiments, each catheter digitizes the electrode outputs in accordance with an internal clock signal. For example, each catheter may comprise an internal clock source (not shown in the figure, may be implemented as part of controller 60) that generates an internal clock signal. This clock signal is used, for example, for clocking MUX 52 and ADC 56. The synchronization process described herein does not involve resetting or otherwise interfering with the internal clock signals of the catheters. In other words, the catheter clock signals may remain free-running regardless of the reception of the synchronization signal or of the synchronization process in general. This feature simplifies the catheter implementation considerably since it eliminates the need for complicated clock manipulation circuitry.

Processor 88 may decide to generate synchronization signals in accordance with any suitable criteria. In some embodiments the processor generates the synchronization signals periodically. The time duration between successive synchronization signals may depend on the rate at which the catheters' internal clocks are expected to drift. As another example, processor 88 may decide to generate a synchronization signal upon detecting that the timing drift between the data packets of different catheters exceeds a certain threshold. This detection can be based, for example, on comparing the packet numbers of data packets arriving from different catheters. In some embodiments the central control unit may combine the two above criteria, i.e., transmit a synchronization signal every predefined time duration, as well as when the timing difference between catheters exceeds a threshold.

Synchronization Method Description

Figure 3:
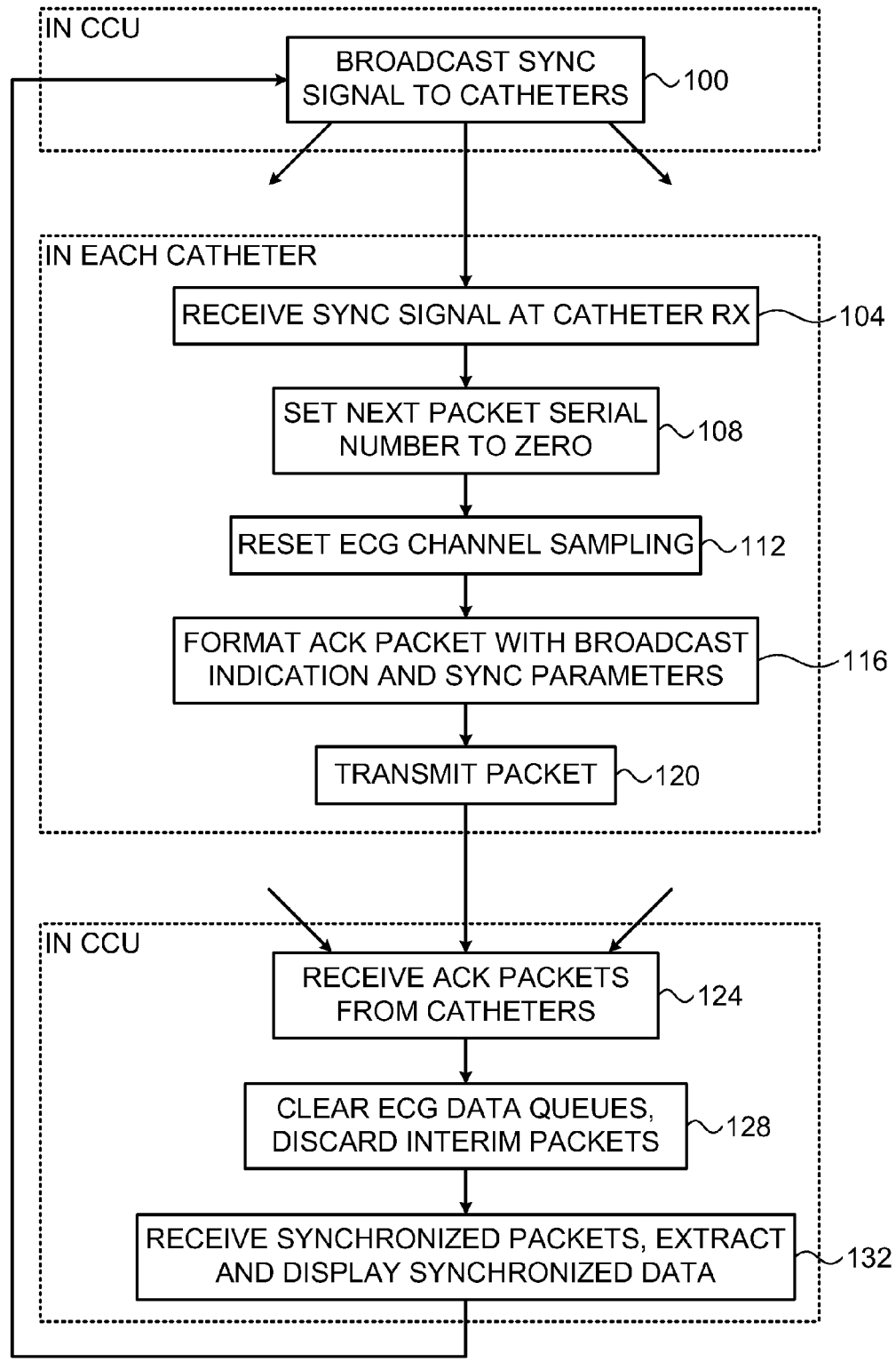
FIG. 3 is a flow chart that schematically illustrates a method for synchronizing multiple catheters, in accordance with an embodiment of the present invention.

FIG. 3 is a flow chart that schematically illustrates a method for synchronizing multiple catheters, in accordance with an embodiment of the present invention. The method begins with central control unit (CCU) 46 broadcasting a synchronization signal to all catheters, at a broadcasting step 100.

Each catheter receives the synchronization signal using receiver 68, at a synchronization reception step 104. In response to the synchronization signal, controller 60 in the catheter resets the packet numbers that are assigned to subsequent data packets, at a packet number resetting step 108. In addition, controller 60 resets the sampling cycle at which the catheter's electrodes are multiplexed, at a cycle resetting step 112. Controller 60 formats an acknowledgement packet to the synchronization signal, at an acknowledgement formatting step 116. As explained above, the acknowledgement packet comprises a "broadcast indication" that acknowledges the reception of the synchronization signal, and one or more synchronization parameters such as the offset parameter.

The catheter transmits the acknowledgement packet to the central control unit using transmitter 64, at an acknowledgement transmission step 120. Steps 104-120 are carried out by any catheter upon receiving the synchronization signal.

Central control unit 46 receives the acknowledgement packets from the different catheters, at an acknowledgement reception step 124. In an embodiment, processor 88 in the central control unit waits until receiving acknowledgement packets from all catheters before proceeding. Upon receiving the acknowledgement packets, processor 88 clears the queues and/or other data structures that are used for storing data packets received from the catheters, at a queue clearing step 128.

In some embodiments, as explained above, processor estimates, using the packet numbers and offset parameters, the maximum relative delay between the catheters. From this maximum delay, processor 88 determines a time period in which arriving data packets may be un-synchronized, and discards such interim packets.

From this stage, processor 88 receives, synchronizes and outputs the data received from the different catheters, at a synchronization step 132. Typically, processor 88 receives data packets from the different catheters, synchronizes the data packets of the different catheters to a common time-base based on the packet numbers and offset parameters, and displays the data in a synchronized manner to physician 24.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
multiple medical probes, each of which probes is configured to acquire physiological data from a living body with which the probe is in contact, to send the data from the probe by transmitting over a wireless channel a sequence of data packets that are marked with respective packet numbers, to receive a synchronization signal that is broadcast to the multiple probes, and, in response to receiving the synchronization signal, to reset the packet numbers that are assigned in the probe to subsequent data packets in the sequence, wherein the synchronization signal does not reset an internal clock of the probes; and
a central control unit, which is configured to transmit the synchronization signal, to receive multiple respective sequences of the data packets from the multiple probes, to time-synchronize the data transmitted in the data packets and to output the time-synchronized data for synchronizing the subsequent data packets.

2. The system according to claim 1, wherein each probe is configured to transmit a respective acknowledgement packet in response to receiving the synchronization signal at the probe, and wherein the central control unit is configured to receive respective acknowledgement packets transmitted by the probes and to time-synchronize the data based on the received acknowledgement packets.

3. The system according to claim 2, wherein each probe is configured to indicate in the respective acknowledgement packet a respective time offset at which the synchronization signal was received at the probe, relative to a data packet produced by the probe.

4. The system according to claim 3, wherein the central control unit is configured to time-synchronize the data based on multiple time offsets indicated in the acknowledgement packets transmitted by the probes.

5. The system according to claim 3, wherein the central control unit is configured to estimate, based on multiple time offsets indicated in the acknowledgement packets transmitted by the probes, a time period during which the data is not synchronized, and to discard the data belonging to the estimated time period.

6. The system according to claim 3, wherein each probe is configured to indicate in the respective acknowledgement packet a respective last packet number of a last data packet that was transmitted from the probe before reception of the synchronization signal, and wherein the central control unit is configured to determine a highest packet number of multiple last packet numbers indicated in the acknowledgement packets transmitted by the probes and to extract the time offset from the data packet having the highest number.

7. The system according to claim 2, wherein the central control unit is configured to present the time-synchronized data to an operator.

8. The system according to claim 1, wherein the central control unit is configured to evaluate a predefined criterion, and to transmit the synchronization signal upon meeting the criterion.

9. The system according to claim 8, wherein the central control unit is configured to evaluate the criterion by estimating a time difference between the multiple probes based on the received data packets, and comparing the time difference to a threshold.

10. The system according to claim 8, wherein the central control unit is configured to transmit the synchronization signal at periodic intervals.

11. The system according to claim 1, wherein the probes comprise intracardiac catheters, and wherein the sensors comprise electrodes that measure electrical signals in a heart.

* * * * *